United States Patent [19]

Tsukamoto

[11] Patent Number: 5,437,606
[45] Date of Patent: Aug. 1, 1995

[54] ULTRASONIC SYSTEM FO ALLEVIATE TOOTHACHES

[76] Inventor: Kenichi Tsukamoto, Beltec Industrietechnik, Rilkestrasse 69, 40668 Meerbusch, Germany

[21] Appl. No.: 218,421

[22] Filed: Mar. 28, 1994

[51] Int. Cl.6 ............................................. A61B 17/22
[52] U.S. Cl. ................................. 601/2; 604/22; 433/86
[58] Field of Search .......... 601/2; 128/660.03, 660.01; 604/22; 433/86

[56] References Cited

U.S. PATENT DOCUMENTS

| Re. 28,752 | 3/1976 | Balamuth et al. | 601/2 |
| 2,874,470 | 2/1959 | Richards | 601/2 |
| 3,375,583 | 4/1968 | Blank et al. | 601/2 |
| 3,380,446 | 4/1968 | Martin | 601/2 |
| 3,645,255 | 2/1972 | Robinson | 601/2 |
| 3,760,799 | 9/1973 | Crowson | 601/2 |
| 3,924,335 | 12/1975 | Balamuth et al. | 601/2 |
| 3,990,452 | 11/1976 | Murry et al. | 601/2 |
| 4,176,454 | 12/1979 | Hatter et al. | 601/2 |
| 4,496,321 | 1/1985 | Kumabe et al. | 433/215 |
| 4,587,958 | 5/1986 | Noguchi et al. | 601/2 |

*Primary Examiner*—Lee S. Cohen
*Assistant Examiner*—Brian L. Casler
*Attorney, Agent, or Firm*—Charles Blaich

[57] ABSTRACT

A method to improve infusion and diffusion of local anesthesia into the gum surrounding a decayed tooth by the application of ultrasound vibration to the hypodermic syringe and needle as local anesthesia is being injected into the gum.

3 Claims, 2 Drawing Sheets

ULTRASONIC SYSTEM FO ALLEVIATE TOOTHACHES

FIELD OF THE INVENTION

The invention relates to an ultrasonic vibrational system that alleviates tooth pains and discomfort, particularly when the tooth is under a dental treatment, such as drilling, filling, reaming, cutting, and anesthetic injection, by applying ultrasonic vibrations directly to a tooth.

BACKGROUND OF THE INVENTION

Even though various theoretical and technical developments have been made in the attempt to reduce or eliminate pains and discomfort during a dental treatment, there remains the fact that no pain transmission mechanism has yet been proved, which might have paved the way to a reliable and safe system. Therefore the process to alleviate the pains consists firstly in the understanding of how pain could be sensed in a diseaded tooth.

Experiments directed to that end, have indicated that tooth pain is connected somehow with the dynamic movement of the dental pulp fluid which is more active in a diseased tooth and less active in a healthy one. Then, the practical method to alleviate the pains during a particular dental treatment, will be to reduce and possibly eliminate those dynamic factors consisting primairly of movement of the dental pulp fluid, that stimulates the nerves. Therefore it is imperative to control this dynamic movement, which has an erratic course, in order to achieve a reduction or elimination of pain, without the use of anesthesia; and in the event that anesthesia is needed, the amount is limited to a small fraction of what is normally used. However, the control of the dynamic movement of the dental pulp fluid requires essentially that the fluid within the dental pulp be saturated, and one way of accomplishing this, is to apply mechanical energy in the form of ultrasonic vibrations, which creates the proper conditions for cavitation to occur.

SUMMARY OF THE INVENTION

The present invention is directed toward a new and improved system to alleviate the pains and discomfort during dental treatment of a tooth, such as a tooth with beginning or advanced caries or other, without or with limited use of anesthesia which can not be used on a great number of patients for a great number of reasons. The apparatus excites a tooth to a frequency and amplitude that create a cavitation effect on the dental pulp fluid, forcing it to the extend that no apparent dynamic movement is experienced within it, thus inducing a partial or total loss of the sense of pain, and consequently a dental treatment can be performed without, or with limited use of anesthesia.

In accordance with the invention, several experiments have been conducted, consisting in applying ultrasonic vibrations directly to a tooth, within the range of frequencies from 40 kHz to 65 kHz. These experiments have clearly indicated that the cavitation effect, a phenomenon well known in physics and engineering, created by the ultrasonic vibration on the dental pulp fluid, causes a saturation and collapse of those microscopic gas bubbles within the fluid, and therefore stabilizing and limiting the erratic dynamic movement of this fluid. As cavitation develops, the gas bubbles, which are apparently responsible for the erratic dynamic movement, collapse as they move into a higher pressure region and this generates powerful local forces, which are affected by the character of the fluid and the gas in it. As a result, the apparent density of the dental pulp fluid increases to a degree where it would not appreciably yield to any change, thus limiting the erratic dynamic movement; it can be viewed also as a tendency of the fluid to remain in its position, similar to the inertia of matter that offers resistance to any change and that remains in the same state unless affected by some outside force. Furthermore, once the dental pulp fluid has been stabilized by the cavitation effect, even though the ultrasonic vibrational energy is removed, it has the tendency to remain in this state, thus prolonging those conditions acting in alleviating pains and discomfort, and it will remain in this state until the gas bubble energy of the dental fluid will dissipate and will return to the previous conditions.

It has been observed in patients a difference in behaviour and in responses to ultrasonic stimulation, because they are affected by the density of the dental pulp fluid, which varies from person to person. It can be said that there is a resemblance to the well known concept for the regulation of human equilibrium, where a denser liquid within a cavity would be causing less dizziness than a lighter one when subjected to motion, such as sea motion. Even though it would be extremely difficult to measure physically and individually the dynamic movement of the dental pulp fluid using the state of the art technology, nevertheless the fundamental concept of the cavitation effect is proven by several lateral ways that lead to its acceptance.

Experiments conducted using frequencies within the range of 40 kHz up to 65 kHz, and amplitudes within 1 um and 10 um, have indicated that tooth pain starts alleviating when a tooth, subject to forced ultrasonic vibration, vibrates at a frequency ranging from 40 kHz to 50 kHz with an amplitude ranging from 3 um to 4 um similarly, the same alleviation effect is found at 60 kHz with amplitude between 1 um and 2 um. However, at a frequency of 60 kHz with amplitude of 3 um to 4 um, and in some cases even up to 9 um, the pain is drastically reduced and can be considered in most cases almost imperceptible. Furthermore, as mentioned previously, the tooth pain is not sensed after removing the horn tip, or at a lesser degree than it was sensed before. It is evident that even though the source of excitation is removed, some of those vibrational forces which acted on the dental pulp fluid, are still present, demonstrating that the cavitation effect does not end with the removing of the vibrational excitation, but it does continue until those forces return to their previous conditions, which are typical for each individual. It must be clear however, that the cavitation effect occurs in a closed space only, that is in a closed area with no connection with the outside, such is the area enveloping the dental pulp fluid.

As mentioned previously, in the event that anesthesia is to be used, because of different patients behavior, the amount of anesthesia would be limited to an amount consisting of only a small fraction of what is commonly used, in many cases only one-tenth of a normal dose, because the narcotic used by injection to relieve pain, is by far more effective when it is subject to ultrasonic vibrational forces. It is evident that the pulsating ultrasonic vibrations, acting on the needle of a syringe or on a diseased tooth after the injection, force the anesthestic fluid to disperse and scatter in all directions, increasing the rate of diffusion, passing into and through, affecting and penetrating those parts which are hard to reach and require exstensive length of time and a large amount of anesthetic fluid to be effective. Furthermore, the anesthetic fluid is attracted by the dynamic center, being the diseased tooth, in which originates the ultrasonic vibrations, thus increasing the permeability of those sensitive parts having pain sensation. In addition, the effectiveness of the anesthetic fluid increases when the horn probe tip is moved around in a circular motion, with light pressure, right on the injection point, similar to massaging and rubbing as to stimulate circulation and penetration of the anesthetic fluid. As a consequence, the time that normally is required for the anesthesia to be effective, which is extensive and varies greatly from person to person, is reduced to only few seconds, and for practical purposes it can be stated that the effectiveness is almost immediate, and the dulling effect, which usually continues and persists for a length of time after a dental treatment, is drastically reduced to sensation so slight as not to be easily perceived. Furthermore, experiments have demonstrated in several instances, that few drops of anesthetic fluid dropped into the dental pulp and applying right after ultrasonic vibrations, were extremely effective, thus avoiding the use of painful injection needles. The benefits those obtained are of inestimable value to human health.

DESCRIPTION OF PREFERRED EMBODIMENTS

The invention will be best understood by reading the following description in connection with the drawings.

Figure 1:
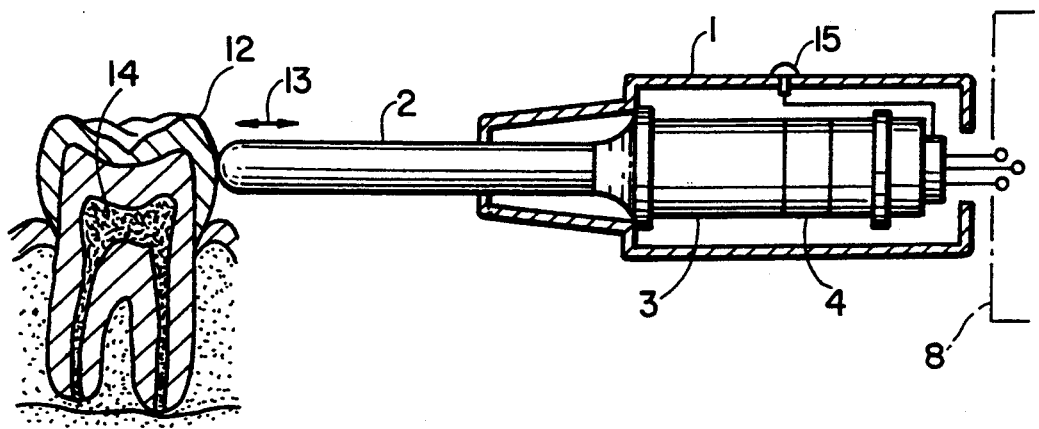
FIG. 1 is a longitudinal view in cross section of the invention.
Figure 2:
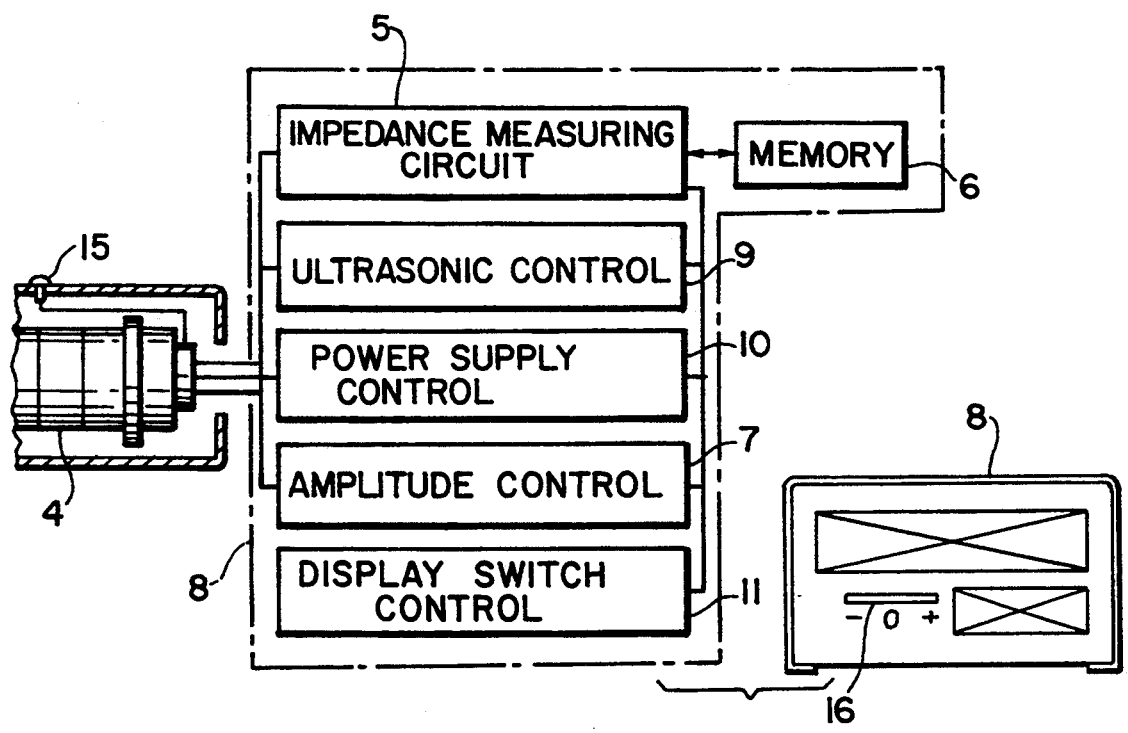
FIG. 2 is a schematic view showing the electronic control system.

FIG. 1 shows an ultrasonic longitudinal vibrator, enclosed in a hand piece 1, disposed on a node of vibration, where electrical vibrational energy is converted into mechanical vibrational energy, which is composed of a vibrator 4, a horn probe 3, shaped in a way to have a tip 2, rounded at the end, that comes into contact with a tooth 12, for imparting ultrasonic vibrations. FIG. 2 shows a control unit 8, which is composed of an impedance measuring circuit 5, an impedance memory 6, an amplitude control 7, an ultrasonic control 9, a power supply control 10, and a display switch control 11. The hand piece 1 is held in a manner that the horn probe tip 2 is being gently pressed against a tooth 12, as indicated by a double-ended arrow 13, so that the ultrasonic vibration is transmitted to the tooth.

Figure 3:
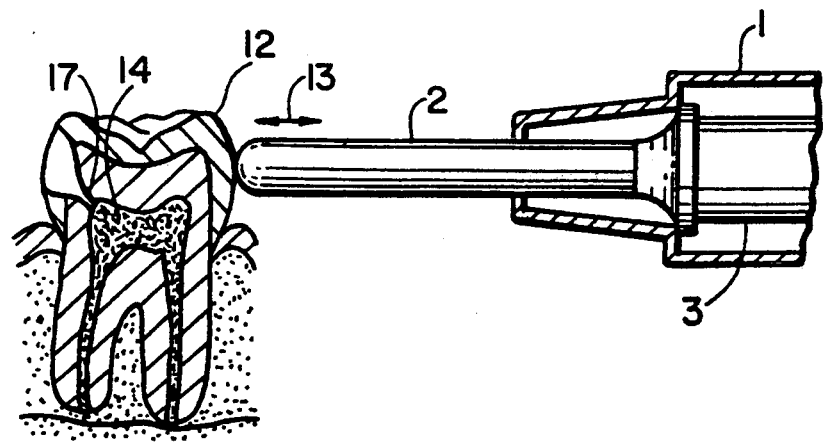
FIG. 3 is a view similar to FIG. 1 but showing a diseased tooth.

Referring to FIG. 3, a small hole 17, created by some form of decay, is shown going through one side of a tooth 12, reaching the upper part of the dental pulp 14, thus allowing a passage between the outside area and the dental pulp in this case, even though ultrasonic vibrations are applied through the horn tip 2 pressed against a tooth 12, the cavitation effect does not occur because the vibrational forces, responsible for the cavitation, cannot create a higher pressure region where gas bubbles are collapsing, being the area open to atmosphere. Therefore tooth pain remains substantially the same, and even with amplitudes varying from 2 um up to 9 um, no appreciable alleviation is experienced, and pain is sensed when air is blown through hole 17. Thus, it is of primordial importance for creating cavitation in a closed area, to control the ultrasonic vibration right on the tooth, which does not vibrate properly if the horn tip 2, imposing the forced vibration, is pressed against the tooth with a force greater or lesser than required. More so, when teeth are drilled, cut, or other, using tools and instruments such as a micromotor characterized by low rpm and high torque requiring generally higher amplitude, the control and the fine adjustment of the amplitude values on the tooth are essential for effective alleviation of pain, because the forces imposed by the cutting instrument being a source of external exitation, cause unbalance which appears and even disappears under certain conditions. It is evident that the amplitude on the tooth is to be tuned to the proper desired performance, similar in a way to a tuner to adjust a radio or television receiver to a specified station.

With reference to FIG. 2, the control unit 8, is composed of a circuitry and instrumentation necessary to control the sympathetic vibration on a tooth. Being the maximum voltage V1 a function of the amplitude, it is calculated from constant current I and impedance Z, and set into the memory 6 of the impedance measuring circuit 5. As the ultrasonic vibrations are forced onto a tooth 12 by the horn probe tip 2 along the direction indicated by the double-ended arrow 13, the tooth starts vibrating with an amplitude controlled by the amplitude control 7. Then the actual impedance Z in the vibrator 4 is measured through the impedance measuring circuit 5, where the actual maximum voltage V is then determined by the well known formula: $V2 = I \times Z$. This measured maximum voltage V2 is thereafter compared to V1 set previously in memory 6, and the result indicates that, whenever V1 is equal to V2 the tooth 12 is vibrating sympathetically with the preset amplitude; however, whenever V1 is not equal to V2 the tooth is not vibrating sympathetically in accordance with the preset value in memory. In this case, in order to evidentiate the difference in amplitude value, the amplitude control 7 activates a warning red lamp 15, located on the hand piece 1, and in addition a leveling LED 16 which offers a vision of the value of deviation, which allows proper adjustment for tuning the amplitude.

Figure 4:
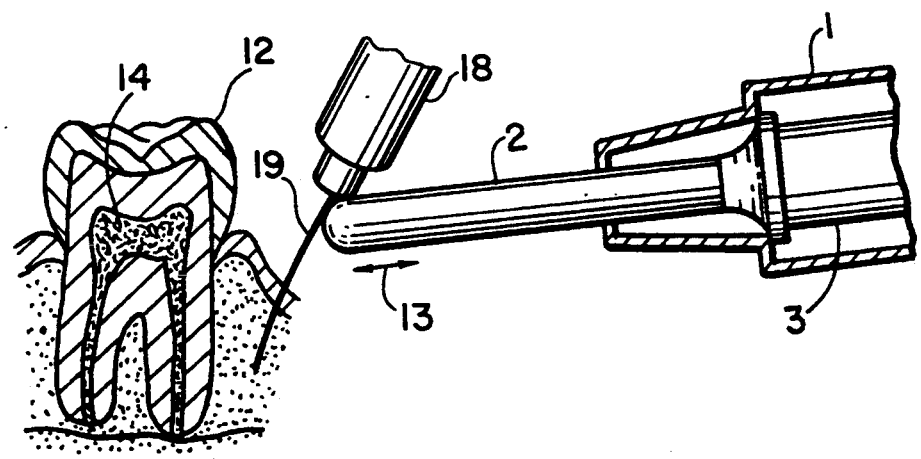
FIG. 4 is a view showing an anesthetic injection.

As shown in FIG. 4, an hypodermic syringe 18 with a hollow metal needle 19, are subject to ultrasonic vibrations during an anesthetic injection, through a horn probe tip 2 being gently pressed, as indicated by a double-ended arrow 13, in order to increase the rate of diffusion and penetration of the anesthetic fluid. The horn probe tip 2 is then moved around with light pressure right on the injection point of the gingiva 20, similar to massaging and rubbing as to stimulate circulation and penetration of the anesthetic fluid.

The invention described above is the result of the ascertainment of the cavitation phenomenon within the dental pulp fluid when it is subject to forced ultrasonic vibrations, the value of which are defined and controlled by an electronic system. The invention is beneficial to human health in alleviating toothaches and reducing drastically the use of narcotic for anesthetic purposes related to dental diseases.

What is claimed is:

1. An improved method of administering local anesthesia to the gum surrounding a decayed tooth comprising injecting a local anesthesia into the gum surrounding a decayed tooth wherein the anesthesia is injected through a hypodermic syringe and needle, applying ultrasonic vibration to said hypodermic syringe and needle containing said local anesthesia by contacting said syringe and needle with an ultrasonic probe as said syringe and needle penetrate said gum, to increase the diffusion of said local anesthesia into said gum surrounding said decayed tooth, said increase in diffusion of said local anesthesia acting to reduce the amount of said anesthesia required to alleviate pain.

2. The method as described in claim 1 further including applying ultrasonic vibration to said decayed tooth to provide additional diffusion of the injected local anesthesia into the gum surrounding the decayed tooth.

3. The method described in claim 1 further including massaging the injection site of said gum with ultrasonic sound vibration to provide additional diffusion of the injected local anesthesia into the gum surrounding the decayed tooth.

* * * * *